(12) United States Patent
Levi

(10) Patent No.: US 7,810,742 B2
(45) Date of Patent: Oct. 12, 2010

(54) ULTRASONIC FOG GENERATOR

(76) Inventor: Zvi Levi, 26 David Elazar Street, PO Box 13381, Rehovot 76100 (IL)

( * ) Notice: Subject to any disclaimer, the term of this patent is extended or adjusted under 35 U.S.C. 154(b) by 132 days.

(21) Appl. No.: 11/751,036

(22) Filed: May 21, 2007

(65) Prior Publication Data

US 2008/0290189 A1   Nov. 27, 2008

(51) Int. Cl.
*B05B 1/08* (2006.01)
*B05B 7/30* (2006.01)

(52) U.S. Cl. .............. 239/102.2; 239/102.1; 239/338; 239/340

(58) Field of Classification Search .......... 239/102.1, 239/102.2, 290, 294, 300, 302, 318, 337, 239/338, 340, 346, 350; 128/200.14, 200.16, 128/200.21; 261/30, 81, DIG. 48

See application file for complete search history.

(56) References Cited

U.S. PATENT DOCUMENTS 5,624,608 A * 4/1997 Ching et al. ............ 261/30

FOREIGN PATENT DOCUMENTS

JP   2004236508 A * 8/2004

* cited by examiner

*Primary Examiner*—Darren W Gorman
(74) *Attorney, Agent, or Firm*—Dekel Patent Ltd.; David Klein

(57) ABSTRACT

An ultrasonic fog generator including a container including therein an ultrasonic nebulizer and a liquid, the ultrasonic nebulizer operative to vibrate at very high frequencies and thereby break down the liquid into a fog including tiny vapor particles, the container having an exit opening for the fog to pass therethrough, and a driver and a driving fluid, the driver being operative to cause the driving fluid to flow past the exit opening and draw out the fog through the exit opening without the driving fluid substantially entering the container.

6 Claims, 3 Drawing Sheets

ULTRASONIC FOG GENERATOR

FIELD OF THE INVENTION

Figure 1:
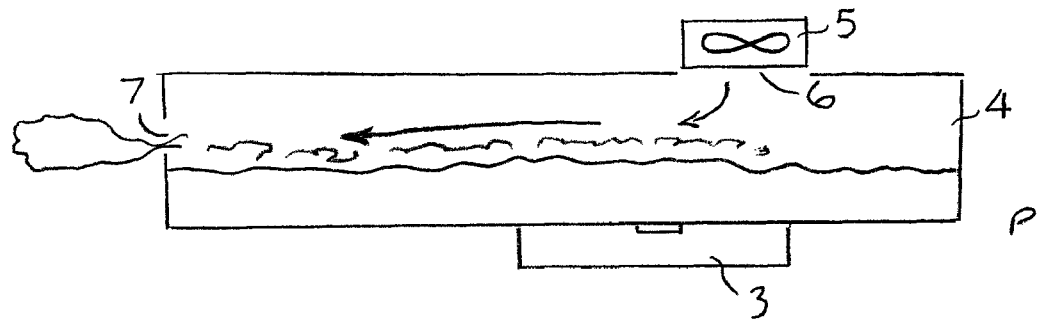

The present invention relates to an ultrasonic fog generator, wherein the fluid that drives the fog outwards to the atmosphere is isolated from the ultrasonic unit that creates the microscopic droplets of liquid.

BACKGROUND OF THE INVENTION

Fog generation by an ultrasonic transducer operating in water is known in the art. A typical ultrasonic fog generator is shown in FIG. 1. An ultrasonic transducer 3 (or ultrasonic wave nebulizer or simply ultrasonic nebulizer, all the terms being used interchangeably throughout the specification and claims) typically includes an oscillator that causes oscillation of an immersed membrane in water in an enclosure 4. The membrane vibrates at very high frequencies, such as but not limited to, 1.7 MHz. The vibration breaks down the water into tiny vapor particles, such as 1-50 microns in diameter or more preferably 1-10 microns. A fan 5 is provided that blows air into enclosure 4 via an inlet port 6. The air blows over the water and carries the tiny vapor particles outwards as a fog mist through an exit port 7. The water vapor particles are so small that they mix with the surrounding air and leave no feel or trace of wetness.

SUMMARY OF THE INVENTION

The bath in which the fog is generated may be closed to influx of air, and may permit using ultraviolet light in the bath to ensure sterility of the fog. The ultrasonic transducer radiates vibrations to create a jet of fog, but does not contact the jet.

The air flow unit may be separate from the bath unit in which the ultrasonic transducer generates the fog and may be placed far away from the transducer/bath unit. The air flow unit draws the fog out without contacting the transducer/bath unit.

The transducer may radiate vibrations in the liquid bath without having to contact upper or side surfaces of the bath, thereby creating a fog jet. The vibrations set up by the transducer generate minute particles of liquid, depending on the frequency of the transducer, such as in the range of KHz that breaks down lime and other hard particles in the liquid or MHz that breaks down other chemicals. It is possible to change the frequency of the transducer, if desired or needed. The air flow unit (fan or blower or gas, etc.) can be placed anywhere and generates an airflow that draws the fog out of the bath unit, which is closed to the atmosphere except for an outlet through which the fog is drawn out. The outlet may be constructed as a one-way outlet so that no fluid enters the bath unit and fog can only escape. The amount of the fog can be controlled. The outlet can be in the form of a tube with one or more holes formed for the fog to escape therethrough. The size of the fog droplets, outlet speed and pressure and other parameters can be controlled.

In the prior art, the ultrasonic transducer is submerged in the liquid bath, produces vibrations that generate microscopic drops of fog at the surface of the liquid. The air flow unit has a limited air velocity that can flow in the liquid bath and blow the fog out to the atmosphere.

The prior art suffers from several drawbacks. The introduction of the air into the bath unit introduces contaminants. The air cannot flow at high velocity over the liquid because too high velocity directly over the liquid interferes with and can even stop the fog production. It is likely that the transducer cannot withstand high temperatures or exposure to chemicals.

In contrast, the invention has many advantages over the prior art.

The transducer of the present invention may comprise a thinner membrane than the prior art. The membrane and all of the transducer has greater longevity than the prior art because it radiates the vibrations to the liquid bath and generates fog without coming into contact with the bath or the fog jet.

The transducer of the present invention is not damaged by chemicals (such as oils or perfumes, antiseptic agents, etc.) because it does not come into contact with them.

The transducer of the present invention may be used in very hot environments because the closed bath unit forms a protected enclosure and the transducer does not come into contact with the heat. The air flow also cools off the unit.

The closed container may prevent air from entering the bath unit. As a result dust may be prevented from entering and direct light may be prevented from impinging on the liquid. This may prevent buildup of microorganisms that can develop especially under light. In addition, there may be an ultraviolet light which by operating in the closed bath may ensure sterility of the fog, something which does not exist in prior art units.

The invention may be used in environments contaminated with pollutants, dirt, and even unpleasant odors. The ultrasonic fog generator may be transported anywhere and used during transportation (rail, marine, truck, etc.).

The invention is not limited to any air flow velocity and can be used anywhere. The invention can provide a wide spectrum of droplet sizes, adapted to any application.

A microphone or other listening device or other appropriate sensor may be disposed near the ultrasonic transducer to detect if the ultrasonic transducer is operating properly or not.

The invention enables many different variations for different applications:

MCA—produces fog containing sterilizing agents/chemicals into ducts, air conditioning systems, heating/cooling systems, small thin tubes, incubators, mist systems and more.

MCT—produces fog containing sterilizing agents/chemicals into rooms, chambers or closets (e.g., for sterilizing clothing stored in closets), and after a certain time, returns the remainders of the fog into the unit for drying and neutralization for reuse, and also the possibility of washing the unit with an automatic jet of water.

MCL—produces fog mixed with gases for sterilization and other purposes, e.g., ozone, ethylene, etc.

MPS—produces fog particles in the range of 1-50 microns for introducing perfumes, fragrances, odorants and agents for neutralizing bad odors in wide open areas and in air conditioning systems, and more.

MPP—produces fog particles as in MPS in any required intensity so that the odorant particles are not stagnant anywhere in the enclosure.

MPN—this is a transportable version of MPS—for mobile systems for producing fog particles as in MPS.

MPA—produces fog particles as in MPS for specific odors, such as coffee smell, flower scents and for absorbing various kinds of odors.

MDS—produces fog and vapor in areas requiring sterile fog in sensitive areas, such as food substances. An ultraviolet light is added to kill microorganisms and ensure sterility of the fog.

MDM—produces fog that circulates in a room or enclosure to produce a controlled atmosphere with no overshoot, especially in sensitive places (e.g., closets and others).

MDA—produces fog and vapor like MDS and can be transported in trucks, ships, planes, etc.

MDC—produces fog and vapor like MDS in conjunction with drying units, air conditioning units, cooling units, steam units, sub-pressure units and others.

MDV—produces fog and vapor for use with air curtains with a spectrum of fog particles. The air curtain so produced has advantages over the prior art:

1. The fog particles are absorbed immediately in the air, increasing the weight of the air and driving the air downwards. This obviates the need for a noisy and high velocity fan at the entrance to the enclosure.

2. The vapor particles of the mist protect the enclosure from excessive cold or heat from entering better than an air curtain without mist.

3. The vapor particles of the mist protect the enclosure from contaminants from entering better than an air curtain without mist.

4. The mist can be augmented by odorants to add fragrance at the entrance or with substances for killing pests, for example.

MDK—(useful in bakeries, textile factories and many more)—produces heated fog controlled to exact temperature and humidity according to the particular application, which prevents overshoot, dew formation, moisture buildup. This aspect of the invention also provides control over distribution of the fog and heat so that the fog is distributed uniformly in all the desired places in the room or enclosure.

MDL—also useful in bakeries, produces mist in an enclosure or room for preserving moisture in food products or for saturating them with moisture from the mist. For example, dough or other products, before entering deep freeze chambers or high temperature chambers, may be exposed to temperature changes that may cause the product to lose moisture to the air. This system produces mist to preserve this moisture before entering the deep freeze or high temperature, thereby enhancing the quality of the food product. The system also provides a more gradual temperature change before entering deep freeze chambers or high temperature chambers.

MDR—produces fog in a freezer at sub-zero temperatures, with possibility of using anti-freeze.

MDC—produces fog/vapor in ducts and tubes, especially for open refrigerated systems, air conditioning systems, etc., and for providing fog in discrete desirable points. This embodiment can be used for yeast curtain systems and chemical/sanitizing systems as well.

MDD—produces fog for getting rid of micron size contaminants, dust, and other particles in the air by means of micron size fog in the desired spectrum that mixes with the bad particles, weighs them down and thus gets rid of them. This embodiment can be used in clean rooms, mist curtain systems and chemical/sanitizing systems as well.

MDF—filters out contaminants, dust, and other particles in the intake of systems, such as air conditioning systems, by means of micron size fog in the desired spectrum that mixes with the bad particles and traps them in a first filter (filter with normal density fibers) and does not let them pass to a second filter (which may also have normal density fibers). This embodiment thus ensures clean running of the system and can be used for air curtain systems and chemical/sanitizing systems as well. One can add sanitizing substances to the liquid.

This solves two problems of the prior art. In some air intakes of prior art systems, filters are used with light density fibers, i.e., the fibers are not tightly packed together. This kind of filter does not overtax the fan but allows contaminants to pass through. Other kinds use very dense filters that trap contaminants, but this causes air flow blockages and overtaxes the fan.

The present invention seeks to provide a novel ultrasonic fog generator, as is described more in detail hereinbelow. In the present invention, the fluid that drives the fog outwards to the atmosphere is isolated from the ultrasonic unit that creates the microscopic droplets of liquid. In this manner, there is no contact between the driving fluid and the liquid at the site of the ultrasonic transducer where the microscopic droplets are formed.

The ultrasonic unit and liquid may be encased in a closed container with an exit opening. The driving fluid may be driven by a blower or fan that uses positive pressure to "push" the driving fluid past the exit opening, and with it, carry the fog out of the bath of the fog generator to the atmosphere. Alternatively, the driving fluid may be provided by negative pressure (suction) that sucks the fog out through the exit opening and out of the unit. The exit opening may be located anywhere on the ultrasonic unit (upper surface, lower surface, sides, etc.).

The closed container prevents direct light from impinging on the liquid, and thus prevents buildup of microorganisms that can develop under light.

The driving fluid may typically be air, but is not limited to this, and ethylene gas may be introduced, for example, in accordance with different requirements of the industry using the fog generator.

The fog may of course be cool or at room temperature. In addition, the driving fluid and/or the fog may be heated to significantly higher temperatures than the prior art. For example, the prior art cannot normally heat the fog above 40° C., because higher temperatures may cause damage to the ultrasonic transducer. In contrast, with the ultrasonic transducer isolated from heating elements, the present invention can easily generate fog at any temperature range to 100° C., for example, and at lower energy costs. The present invention thus generates ultrasonic fog independently and separately from heating the fog. As a result, unlike the prior art, the present invention can control the temperature separately from the humidity (i.e., the amount of vapor that exits to and mixes with the atmosphere). The present invention thus eliminates the problem of "overshoot" that plagues some prior art systems, in which there is no control over the relation between humidity and temperature and in which excessive humidity can develop or surges of oversized droplets that leave surfaces wet for microorganisms to develop, or which can cause damage to produce or other items, or which can clog up equipment (e.g., filters).

The present invention has many advantages and improvements over the prior art. For example, the isolation between the driving fluid and the ultrasonic unit vastly diminishes or eliminates contamination of the ultrasonic fog, because any contaminants (e.g., microorganisms, dirt, foreign particles, etc.) are not introduced into the ultrasonic unit. The present invention also diminishes or eliminates the need for filters to filter the driving fluid. This may be important for applications where filters should not be used, such as humidifiers where a filter would get quickly clogged. The isolation permits using significantly faster velocities and/or volumetric flows of the driving fluid than the prior art. The invention greatly expands the range and kind of fluid flow that can be used by the driving fluid to drive the fog out of the unit, such as but not limited to, vortex flows, crisscross flows, flow through small diameter tubes (which the prior art does not have the pressure head to cause the fog to pass through) and many others. The wide range of fluid flows means that the present invention can distribute the ultrasonic fog much more efficiently to all parts of a room than the prior art. For example, the present invention can be used to uniformly distribute fog to stacks of baking trays/shelves in a bakery, thereby ensuring that all baked goods on the trays/shelves receive the benefits of the moist fog.

The invention may be used in environments contaminated with pollutants, dirt, and even unpleasant odors. In the latter case, the driving fluid may be passed through a unit that neutralizes odors and then passed over a unit that emits pleasant fragrances and odors. Alternatively or additionally, sterilizing agents may be introduced by means of the driving fluid into the fog.

The invention may be used in environments with chemicals, corrosive solids, liquids or gases, because the hazardous materials do not come into contact with the transducer. Different embodiments of the invention may be used for distribution of mist that contains chemicals (e.g., ozone or ethylene for sterilization) into ducts, air conditioning units, heating/cooling units, etc., and into thin tubing. Other embodiments may be used for distribution of mist that contains chemicals (e.g., for sterilization) into room or other enclosure. The apparatus of the invention may suck back remainders of the mist from the room to neutralize odors and other unwanted properties or particles The ultrasonic fog generator may be transported anywhere and used during transportation (rail, marine, truck, etc.).

The invention can provide a wide spectrum of droplet sizes. Additionally, the invention may be used with any kind of droplet formation devices, such as but not limited to, carbureting devices, diesels, nozzles, sprayers, etc., in fluid communication with the nebulizer and which modify the size of the droplets.

The invention may be used to form a "curtain" of mist to prevent entrance of dust and other contaminants to an enclosure. For example, the apparatus of the invention may be placed near the entrance to a "clean" room (e.g., microelectronics assembly room), at the top part of the entrance, lower part or other position, and expel a mist that absorbs dust and other contaminants and prevents them from entering the enclosure. As another example, the apparatus of the invention may be placed near the entrance to an air conditioned or refrigerated room, at the top part of the entrance, lower part or other position, and expel a mist that absorbs moisture, water particles and/or humidity. The mist becomes heavier after absorbing the water and tends to drop towards the floor and not enter the room. This helps keep out hotter air from entering the refrigerated room and helps keep the room cooler. Alternatively, the "mist curtain" can be used in a heated room to keep cold air from entering and hot air from escaping. The "mist curtain" can be used to add smells or fragrances at the entrance to the room, or substances that kill or prevent insects or other creatures from entering the room.

The invention may be used to form mist that has been mixed with soluble powders, smoke effect particles and other stage effect particles, and fertilizer particles, etc.

The invention may be used to increase humidity in dry areas (e.g., rooms, closets, etc.) without causing wetness problems. The invention may be used to clean lenses, gems and other sensitive surfaces.

Throughout the specification and claims, the terms "mist" and "fog" are used interchangeably.

BRIEF DESCRIPTION OF THE DRAWINGS

The present invention will be understood and appreciated more fully from the following detailed description, taken in conjunction with the drawings in which:

FIG. 1 is a simplified illustration of a prior art ultrasonic fog generator;

FIG. 2 is a simplified schematic illustration of an ultrasonic fog generator, constructed and operative in accordance with an embodiment of the present invention, in which a blower or similar device drives fog with positive pressure out to the atmosphere;

FIG. 3 is a simplified schematic illustration of an ultrasonic fog generator, constructed and operative in accordance with another embodiment of the present invention, in which a blower or similar device sucks fog with negative pressure out to the atmosphere;

FIG. 3A is a simplified schematic illustration of an ultrasonic fog generator, constructed and operative in accordance with another embodiment of the present invention, in which the driving fluid passes through a tube placed over the ultrasonic transducer;

FIG. 4 is a simplified schematic illustration of an ultrasonic fog generator, constructed similarly to the embodiment of FIG. 3, including a manifold and tubing for distributing the fog to different destinations, in accordance with an embodiment of the present invention;

FIG. 5 is a simplified schematic illustration of an ultrasonic fog generator, constructed and operative in accordance with yet another embodiment of the present invention, in which fog is expelled to a rack of items; and FIG. 6 is a simplified schematic illustration of an ultrasonic fog generator, constructed and operative in accordance with an embodiment of the present invention, in which fog is used as an air-fog curtain.

DETAILED DESCRIPTION OF EMBODIMENTS

Reference is now made to FIG. 2, which illustrates an ultrasonic fog generator 10, constructed and operative in accordance with an embodiment of the present invention.

The ultrasonic fog generator 10 may include a container 12 including therein an ultrasonic nebulizer 14 and a liquid 16, such as but not limited to, water. The ultrasonic nebulizer 14 is commercially available from many manufacturers and can vibrate at very high frequencies (such as but not limited to, a frequency range of 1.5-2.5 MHz) and thereby break down the liquid into a fog 18 including tiny vapor particles (such as but not limited to, 1-50 microns in diameter). The container 12 may have an exit opening 20 for the fog 18 to pass therethrough. The exit opening 20 may be a single opening or multiple openings. The container 12 is preferably sufficiently closed to prevent direct light from impinging on the liquid 16, and thus prevents buildup of microorganisms that can develop under light. The container 12 may include an ultraviolet (UV) light 17 that may help inhibit growth of, or sterilize or destroy, microorganisms that perhaps entered the container 12 or which may have developed in the dark or for any other reason. The exit opening 20 may be located anywhere on the container 12 (upper surface, lower surface, sides, etc.).

A driver 22 may be provided for causing a driving fluid 24 to flow past the exit opening 20 and draw out the fog 18 through the exit opening 20 without the driving fluid 24 substantially entering the container 12. The driver 22 may include, without limitation, a blower or fan (the terms being used interchangeably throughout the specification and claims) or sprayer or any other suitable apparatus. The driving fluid 24 may include, without limitation, air or air mixed with ethylene or other gases or liquids and any combination thereof. The driver 22 may be placed close to container 12 (or in or on container 12) or may be remote from container 12.

In the present invention, there is no contact between the driving fluid 24 and the liquid 16, thus preventing contamination of the liquid 16 and the fog 18.

Figure 2:
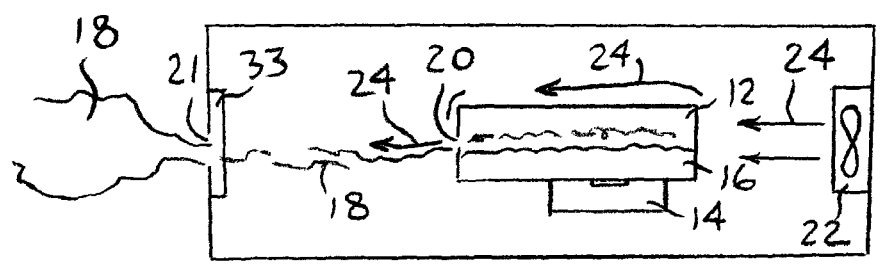

In the embodiment of FIG. 2, for example, the driver 22 includes a blower that uses positive pressure to drive the driving fluid 24 past the exit opening 20 and drive the fog 18 out of the container 12 and through an exit port 21. Various filters 33 may be used, if desired, to filter contaminants while exiting port 21.

Figure 3:
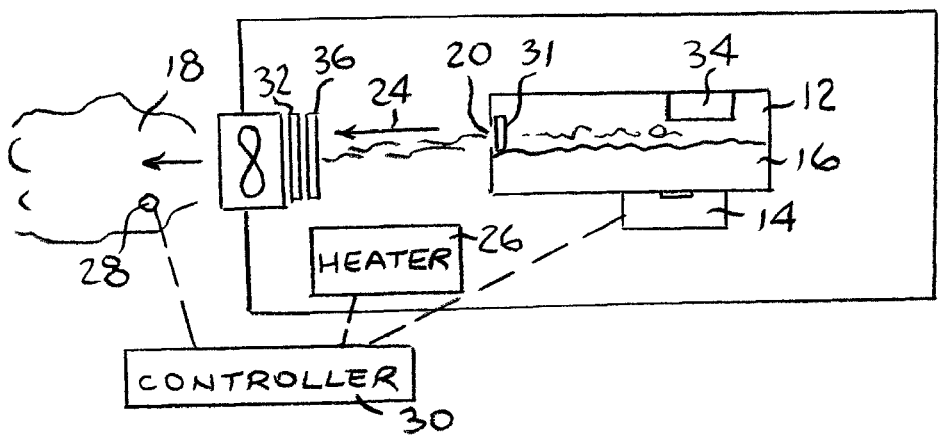

In the embodiment of FIG. 3, the driver 22 includes a blower that uses negative pressure to drive the driving fluid 24 past the exit opening 20 and suck the fog 18 out of the container 12.

The fog 18 may of course be cool or at room temperature. In another option, as shown in FIG. 3, a heater 26 may be provided which is separated from the container 12 and the ultrasonic nebulizer 14. Heater 26 may be any kind of heating element, such as but not limited to, an electric resistance heating element, a thermoelectric element, a combustion heater, a heat exchanger and the like. Heater 26 may heat the driving fluid 24 and/or the fog 18 to significantly higher temperatures than the prior art. For example, the prior art cannot normally heat the fog above 40° C., because higher temperatures may cause damage to the ultrasonic transducer. In contrast, the present invention generates fog independently and separately from heating the fog. Heater 26, which is isolated from ultrasonic transducer 14, can easily heat the fog 18 to its boiling point (e.g., 100° C.) and at lower energy costs than the prior art.

The ultrasonic fog generator 10 may further include a sensor 28 that senses temperature (e.g., a thermocouple or thermistor) and/or humidity (e.g., hygrometer). The sensor 28 may be in communication with a controller 30 (e.g., microprocessor) adapted to control operation of heater 26 and/or ultrasonic nebulizer 14 in accordance with information sensed by the sensor 28. As a result, unlike the prior art, the present invention can control the temperature separately from the humidity (i.e., the amount of vapor that exits to and mixes with the atmosphere). The present invention thus eliminates the problem of "overshoot" that plagues some prior art systems, in which there is no control over the relation between humidity and temperature and in which excessive humidity can develop or surges of oversized droplets that leave surfaces wet for microorganisms to develop, or which can cause damage to produce or other items, or which can clog up equipment (e.g., filters).

Controller 30 may also control a valve 31 positioned at exit opening 20. Valve 31 (which may be solenoid operated, for example) may be any kind of suitable valve, such as but not limited to, a butterfly valve or a one-way valve. By controlling valve 31, controller 30 can control the amount of fog 18 exiting exit opening 20.

Another option is shown in FIG. 3. A deodorizing unit 32 may be positioned relative to the driver 22, which deodorizes the driving fluid 24 used to drive the fog 18 out of the container 12. The deodorizing unit 32 may be, without limitation, charcoal filters or a liquid through which odor-containing air is scrubbed or bubbled through a liquid that dissolves or emulsifies the odorous molecules.

Further options are shown in FIG. 3. For example, a fragrance unit 34 may be provided that imparts a fragrance (smell, scent or odor, all the terms being used interchangeably throughout the specification and claims) to the fog 18. The fragrance may be that of coffee, flowers, perfume, etc., for imparting a pleasing odor to a room or for aromatherapy, for example. Additionally or alternatively, a sterilizing agent 36 may be provided that sterilizes the driving fluid 24 and/or fog 18.

Figure 3A:
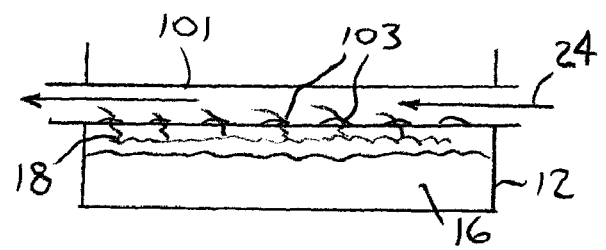

Reference is now made to FIG. 3A, which illustrates another option of the ultrasonic fog generator, in accordance with another embodiment of the present invention. In this embodiment, the driving fluid 24 passes through a tube 101 with a plurality of openings 103 placed over the liquid 16 in container 12. The driving fluid 24 forces (e.g., sucks or blows) the fog 18 into the tube 101 through openings 103. The openings 103 may be on the sides of the tube 101, but may be in other places as well. Here again, there is no contact between the driving fluid 24 and the liquid 16, thus preventing contamination of the liquid 16 and the fog 18.

Figure 4:
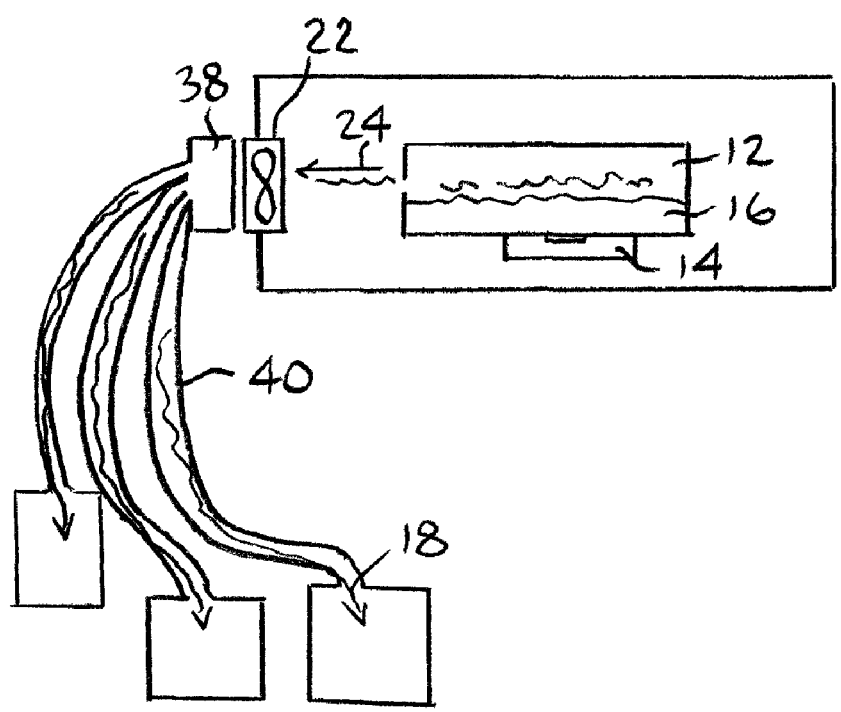

Reference is now made to FIG. 4, which illustrates another version of ultrasonic fog generator 10, including a manifold 38 and tubing 40 for distributing the fog 18 to different destinations, such as but not limited to, vegetable and fruit bins in a supermarket or different storage areas of pharmaceuticals. As mentioned above, since the driving fluid 24 is isolated from container 12, significantly faster velocities and/or volumetric flows of the driving fluid 24 may be used, which provides the pressure head to cause the fog 18 to pass through tubing 40.

Figure 5:
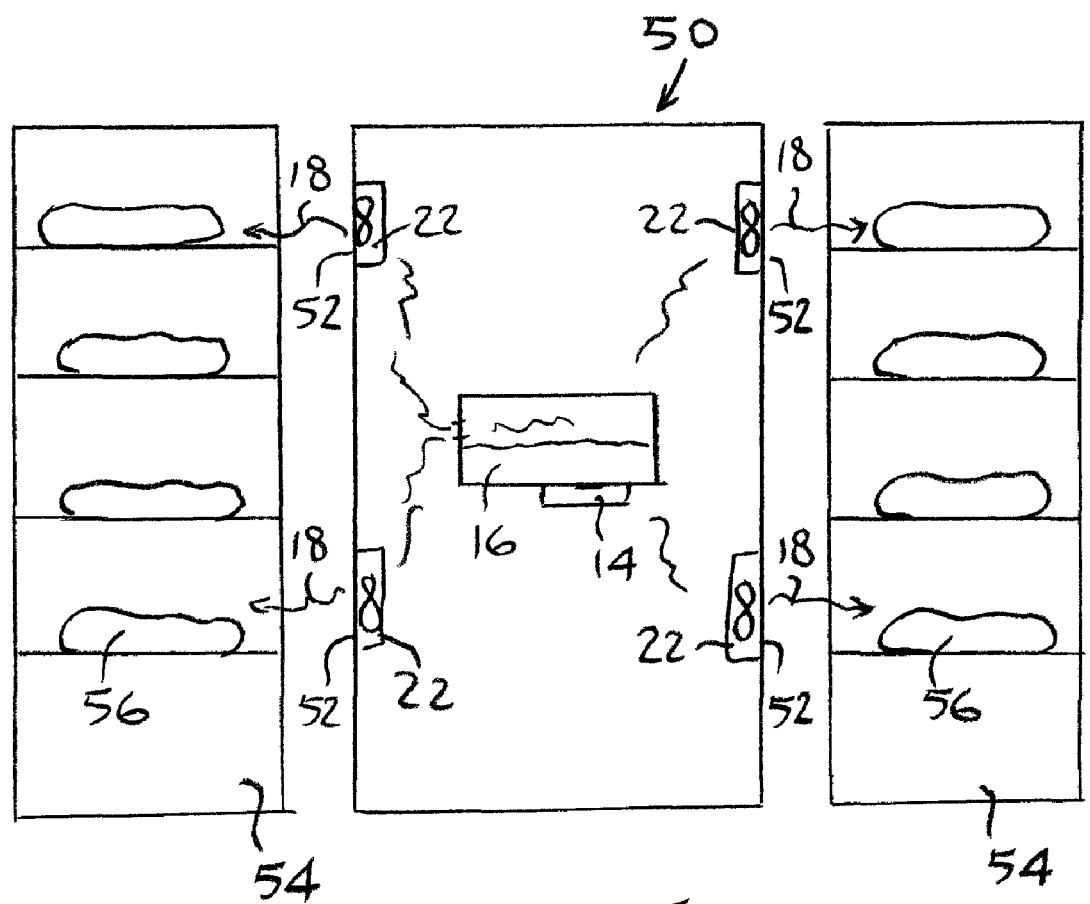

Reference is now made to FIG. 5, which illustrates another ultrasonic fog generator 50, constructed and operative in accordance with an embodiment of the present invention. Ultrasonic fog generator 50 may include several outlets 52 for expelling fog 18 to a rack 54 of items 56, such as but not limited to, a stack of baking shelves (or tray or racks, the terms being used interchangeably throughout the specification and claims) on which loaves of bread or other baked goods are placed after baking in an oven (not shown). The fog 18 may be heated and the humidity and temperature may be regulated as described hereinabove.

Figure 6:
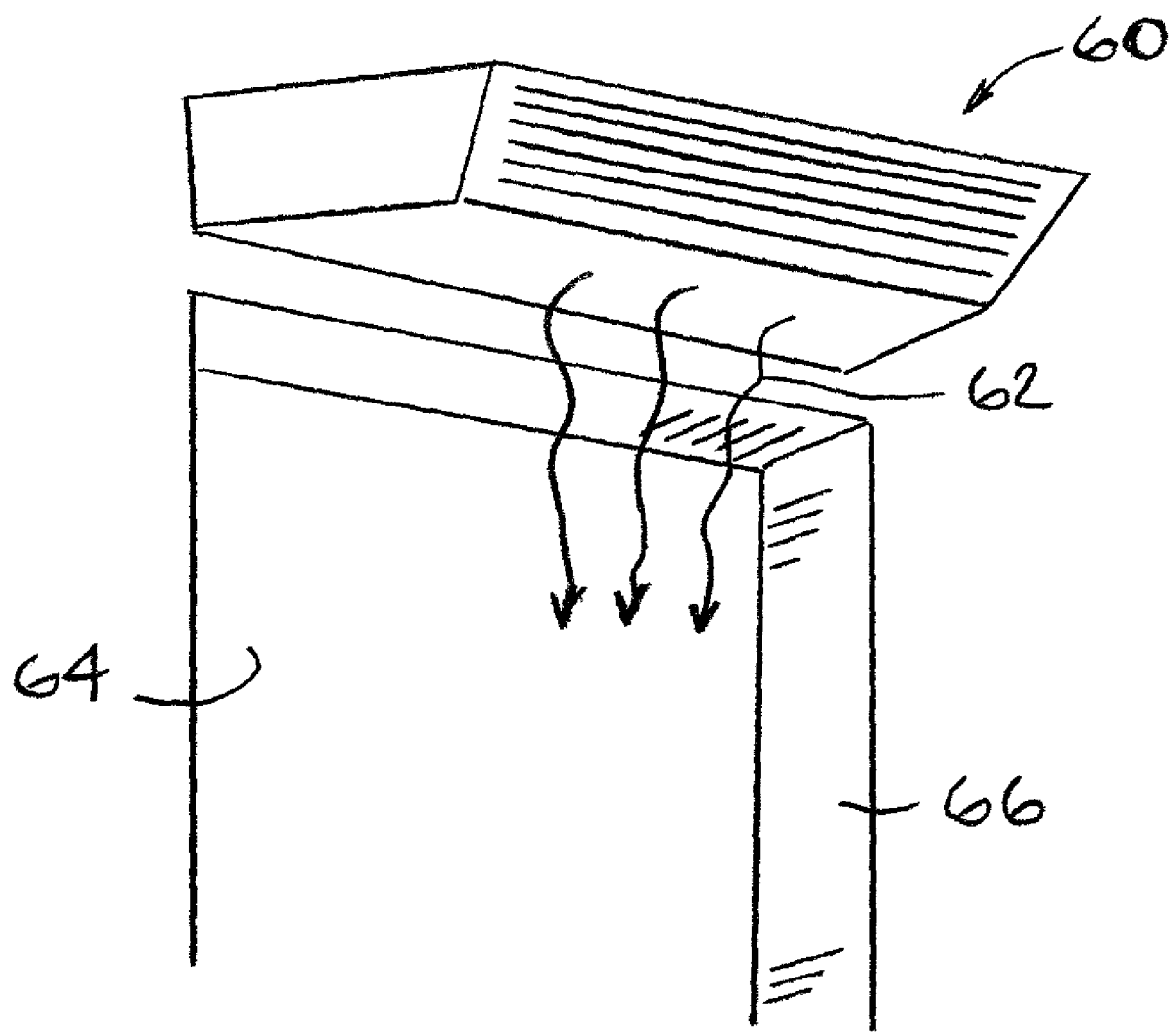

Reference is now made to FIG. 6, which illustrates an ultrasonic fog generator 60, constructed and operative in accordance with an embodiment of the present invention, in which fog is used as an air-fog curtain.

Fog generator 60 may be constructed as described hereinabove for fog generator 10. Fog generator 60 may be used to form a "curtain" of mist 62 to prevent entrance of dust and other contaminants to an enclosure 64. For example, the apparatus of the invention may be placed near an entrance 66 to enclosure 64, such as but not limited to, a "clean" room (e.g., microelectronics assembly room), at the top part of the entrance, lower part or other position, and expel mist 62 that absorbs dust and other contaminants and prevents them from entering the enclosure. As another example, enclosure 64 may be an air conditioned or refrigerated room, and the fog generator 60 may be placed at the top part of the entrance 66, lower part or other position, and expel mist 62 that absorbs moisture, water particles and/or humidity. The mist 62 becomes heavier after absorbing the water and tends to drop towards the floor and not enter the room. This helps keep out hotter air from entering the refrigerated room and helps keep the room cooler. Alternatively, the "mist curtain" can be used in a heated room to keep cold air from entering and hot air from escaping. The "mist curtain" can be used to add smells or fragrances at the entrance to the room, or substances that kill or prevent insects or other creatures from entering the room.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. An ultrasonic fog generator comprising:

a container comprising therein an ultrasonic nebulizer and a liquid, said ultrasonic nebulizer operative to vibrate at very high frequencies and thereby break down the liquid into a fog comprising tiny vapor particles, said container having an exit opening for said fog to pass therethrough;

a driver and a driving fluid, said driver being operative to cause said driving fluid to flow past the exit opening and draw out said fog through the exit opening without said driving fluid substantially entering said container, wherein said driver is positioned facing a closed rear face of said container and said exit opening is positioned on a front face of said container opposite said rear face, wherein said front face of said container comprises a wall extending from side faces of said container, and said exit opening is formed through said wall.

2. The ultrasonic fog generator according to claim 1, wherein said ultrasonic nebulizer vibrates in a frequency range of 1.5-2.5 MHz.

3. The ultrasonic fog generator according to claim 1, wherein said ultrasonic nebulizer is operative to break down the liquid into fog comprising tiny vapor particles of 1-50 microns in diameter.

4. The ultrasonic fog generator according to claim 1, wherein said driver uses positive pressure to drive the driving fluid past the exit opening and drive the fog out of the container.

5. The ultrasonic fog generator according to claim 1, wherein said container is sufficiently closed to prevent direct light from impinging on the liquid.

6. The ultrasonic fog generator according to claim 1, wherein said driving fluid flows from said driver over side faces of said container spanning an entire length of said container.

* * * * *